United States Patent [19]

Stoller

[11] 4,208,602
[45] Jun. 17, 1980

[54] PIEZOELECTRIC ULTRASONIC SCANNING HEAD USING A BERYLLIUM MIRROR

[75] Inventor: Milton Stoller, West Hartford, Conn.
[73] Assignee: Mediscan, Inc., South Windsor, Conn.
[21] Appl. No.: 4,392
[22] Filed: Jan. 18, 1979
[51] Int. Cl.² ............................................. H01L 41/10
[52] U.S. Cl. ..................................... 310/335; 73/620; 128/660; 310/336; 310/369
[58] Field of Search ................................ 310/334–337, 310/339; 73/596, 605–608, 620, 627, 629, 632, 660, 24 A; 340/8 RT

[56] References Cited

U.S. PATENT DOCUMENTS

| | | | |
|---|---|---|---|
| 3,251,219 | 5/1966 | Hertz et al. | 128/660 X |
| 4,084,582 | 4/1978 | Nigam | 73/620 X |
| 4,137,777 | 2/1979 | Haverl et al. | 128/660 X |
| 4,143,554 | 3/1979 | Nagy et al. | 73/620 X |

OTHER PUBLICATIONS

European Published Application, EP-00-067, Dec. 1968, New York Institute of Technology.

*Primary Examiner*—Mark O. Budd

[57] ABSTRACT

A beam of ultrasonic energy is scanned through the use of a steerable mirror positioned in a liquid path traversed by the beam between a transmit-receive crystal and the target. The mirror is comprised of a material selected to have an angle of excitation of surface waves at the liquid-mirror interface which lies outside the range of angles of transmission and reception incidence at which the beam impinges on the mirror.

10 Claims, 1 Drawing Figure

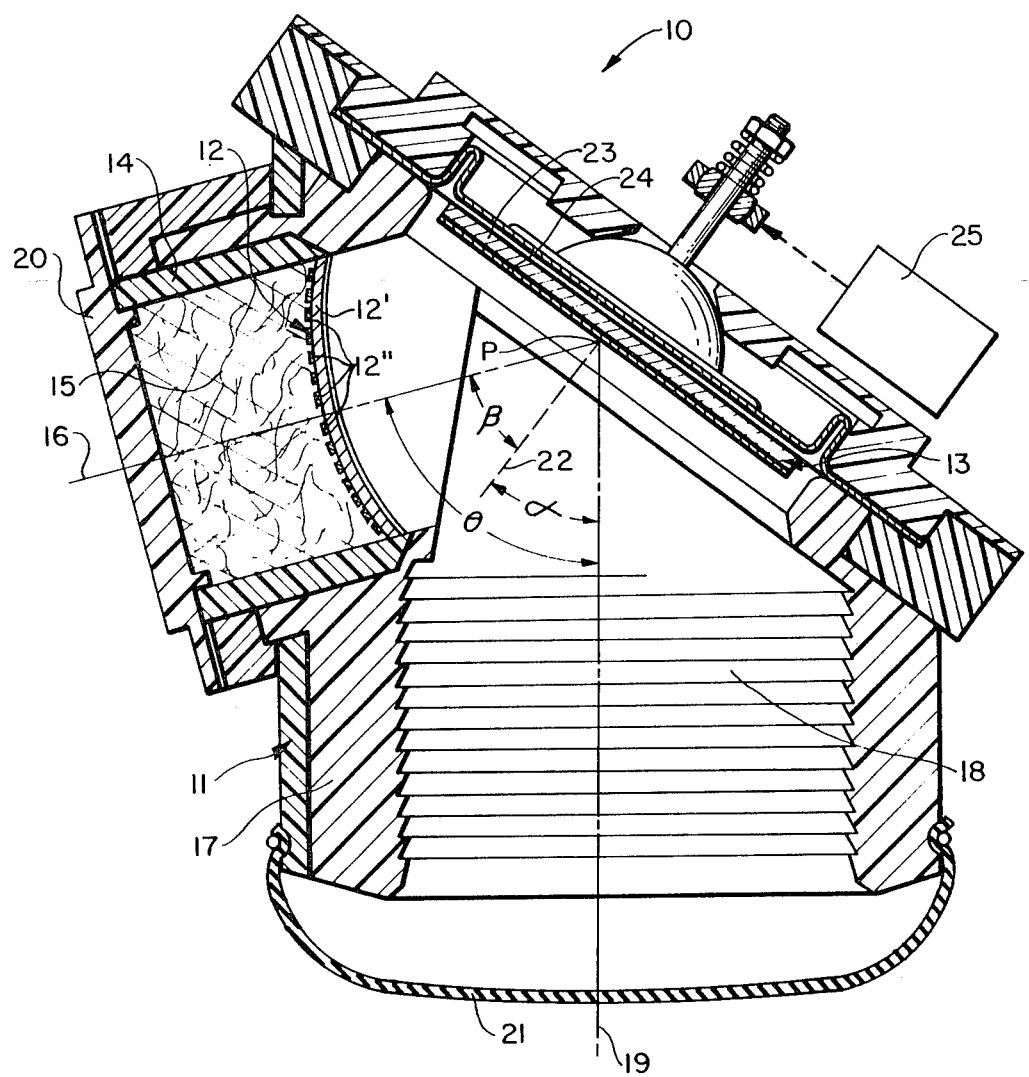

PIEZOELECTRIC ULTRASONIC SCANNING HEAD USING A BERYLLIUM MIRROR

BACKGROUND OF THE INVENTION (1) Field of the Invention

The present invention relates to non-destructive testing and particularly to the non-invasive examination of soft tissue and body organs. More specifically, this invention is directed to medical ultrasonic equipment and particularly to pulse-echo body scanners employing driven mirrors. Accordingly, the general objects of the present invention are to provide novel and improved methods and apparatus of such character.

(2) Description of the Prior Art

Apparatus and techniques which permit the non-invasive examination of bodies through the use of ultrasonic energy are well known in the art. A persistent problem in prior art ultrasonic test equipment is that spurious signals may provide false, inaccurate or unclear readings.

One source of spurious energy in an ultrasonic transceiver of the type employed for medical diagnostic purposes is beam "displacement" which may occur when the focused ultrasonic energy, which is transmitted through a liquid, is incident upon the liquid-solid interface at the mirror employed to scan the beam over a target area of interest. The principle of "displacement" of an ultrasonic beam when it is reflected from a liquid-solid interface is disclosed in Breazeal, Adler and Flax, "Reflection of a Gaussian ultrasonic beam from a liquid-solid interface", J. Acous, Soc. Am., Vol. 56, No. 3, September 1974. As set forth in this article, "beam displacement" occurs when the angle of incidence of the beam is the same as or near the angle of excitation of surface waves on the interface. Experimental test results reported in the aforementioned article show that the energy of the reflected beam may be redistributed into two or more separate beams which are displaced from one another. As will be appreciated by those skilled in the art, redistribution of the energy incident on the scanning mirror into two or more displaced beams is undesirable. The thus "displaced beams" will be reflected from the body to be tested and, after redirection by the mirror, will be incident on the transducer crystal. Since the original and "displaced" energy will travel different distances, the signal transduced by the receiver crystal is likely to lack clarity. Thus, it is the principal object of the present invention to reduce or avoid reception of spurious ultrasonic energy by the receive transducer of an ultrasonic test device.

SUMMARY OF THE INVENTION

The present invention overcomes the above briefly discussed and other deficiencies and disadvantages of the prior art and in doing so provides a novel scanning head for an ultrasonic test device. The scanning head of the present invention comprises a body which defines a transducer passage having a first axis. A transducer crystal, which will usually be employed as both the ultrasound generator and the receiver, is positioned within the transducer passage and provides a beam of ultrasonic. The body also includes a transmission-reception passage which defines a second axis. The transducer passage communicates with the transmission-reception passage and, preferably, the first and second axes intersect at a point. The passages are filled with a liquid to minimize attenuation of the ultrasound energy. The axes of the passages are positioned with respect to each other at an angle of less than 90° and the length of each of the passageways is sufficient to block the direct travel of ultrasonic energy from the target to the transducer.

The transducer crystal, due to its physical configuration and/or mode of excitation, generates a focused beam of ultrasonic energy. A scannable mirror is positioned at the junction of the two aforementioned passages and the axes of the passages intersect at a point on the surface of the mirror. In a preferred embodiment this is also the point about which the mirror pivots during scanning. Furthermore, the axis of the beam provided by the transducer, in the preferred embodiment, is coincident with the axis of the transducer passage.

A pulse of ultrasonic energy directed toward the mirror will be incident thereon at an angle which may be referred to as the "transmission angle of incidence". A portion of the pulse of ultrasonic energy directed by the mirror into the target is reflected back toward the mirror and impinges the mirror at an angle which will be termed the "angle of reception incidence". As the ultrasonic scanning head functions, the mirror is pivoted about the point of intersection of the passage axes and the angles of transmission incidence and reception incidence vary.

In accordance with the invention, the mirror is comprised of a material which has an angle of excitation of surface waves on the interface outside the range of transmission and reception incidence angles which result from the scanning of the mirror.

In order to avoid functioning in a range of incident angles which includes the angle of excitation of surface waves on the interface, beryllium is selected as the material for the mirror in the preferred embodiment; the angle of excitation of surface waves on the interface for a beryllium/water interface being approximately 11°. Thus, the ultrasonic scanning head is devised so that the range of incident angles, either the transmission incidence or the reflection incidence, does not include 11°.

Other objects and advantages of the present invention will be apparent from the following detailed description of the invention.

BRIEF DESCRIPTION OF THE DRAWINGS

The present invention may be better understood and its numerous objects and advantages will become apparent to those skilled in the art by reference to the accompanying drawing which is a cross-sectional view of an ultrasonic scanning head in accordance with a preferred embodiment of the invention.

DETAILED DESCRIPTION OF THE INVENTION

Referring to the FIGURE, ultrasonic scanning head 10 comprises a body indicated generally at 11. The principal elements of the scanning head are the transducer and mirror, respectively indicated generally at 12 and 13, which are positioned in body 11. Body 11 includes a transducer housing portion 14 which defines a passage 15. Passage 15 has a longitudinal axis 16. Body 11 also includes a transmission and reception portion 17 which defines a transmission and reception passage 18 having a longitudinal axis 19. Passage 15 and 18 are in communication and the axes of the passages intersect at a point P. Housing portion 14 is sealed with end cap 20 and passage 18 terminates in a resilient bladder 21; the bladder being adapted to be placed in contact with the irregular surface of an article to be scanned. Mirror 13 is positioned so that a point on the surface of the mirror is coincident with point P. The passages; that is, the space between the transducer 12 and bladder 21; is filled with a liquid such as deaerated water. The face of mirror 13 from which the ultrasound energy is reflected is immersed in the liquid.

Transducer 12 preferably comprises a piezoelectric crystal 12' having a natural focal length and energized by a phased coaxial array of electrodes 12". The means for delivering drive signals to electrodes 12" has been omitted from the drawing but would include conductors which pass through cap 20. Transducer 12, when electrically stimulated, provides an ultrasonic energy beam having an axis which is coincident with axis 16 of passage 15. The axis of the ultrasonic energy beam is directed to point P and the beam is reflected through passage 18 to the object to be scanned. The mirror is pivoted about point P by a drive system 25 whereby the beam reflected from the mirror scans the target area of the test object. For a discussion of means for driving mirror 13, reference may be had to co-pending application Ser. No. 814,477, now U.S. Pat. No. 4,137,777 issued Feb. 6, 1979.

The ultrasonic energy directed into the body to be tested is reflected from the interior portions of the body and directed once again toward mirror 13. The ultrasound energy is reflected from the mirror and impinges upon transducer crystal 12' which converts the returned energy into electrical signals.

It should be understood that, during the travel of the beam from the mirror to the test object and the travel of the reflected energy from within the test object back to the mirror, spurious ultrasonic energy may be generated as the beam encounters interfaces between materials having different accoustic impedance. It is desirable to reduce or eliminate spurious ultrasonic energy which would be returned to the transducer by other than a direct path which includes the mirror 13. In order to screen the transducer 12 from at least a portion of the spurious ultrasonic energy, axis 16 of transducer passage 15 is disposed at an angle, $\theta$, less than 90°, with respect to the axis 19 of the transmission and reception passage 18. In one reduction to practice the angle $\theta$ is 75°. Thus, spurious ultrasonic energy reflected at the surface of bladder 21 or the target surface are absorbed by the irregularly shaped interior surfaces of body 11 of the scanning head. Body 11 of the scanning head will preferably be made from a plastic material characterized by relatively high absorption of the ultrasonic energy at the wavelength used.

The angle between the axis of the beam emitted from transducer 12 and the surface of undeflected mirror 13 at point P is indicated at $\beta$; this being shown as the angle between a line 22 drawn through point P and perpendicular to the undeflected mirror and the axis of the beam generated by transducer 12. The angle $\beta$ is defined as the "angle of transmission incidence". The angle $\alpha$ is defined as the angle of incidence of a beam that has been reflected from the target and directed back toward point P on the mirror, that is, the "angle of reception incidence". As the mirror is tilted, the angles $\alpha$ and $\beta$, vary. In accordance with the present invention, mirror 13 is formed from a material selected to have an inherent angle for the excitation of surface waves on the interface between the mirror and the liquid disposed within passages 15 and 18 which is outside of the range over which the angles of incidence and reflection, that is angles $\beta$ and $\alpha$, vary. It has been determined that beryllium has an angle for the excitation of surface waves on an interface with water which is approximately 11°. Thus, by using a mirror comprising beryllium and water as the transmission medium, the angles of transmission incidence and reception incidence may vary in a range which is outside of the inherent angle for the excitation of surface waves on the interface present in beryllium while still providing adequate scanning capability.

Mirror 13 comprises a body 23 of beryllium. The beryllium portion or base 23 of mirror 13 should have a thickness which is a function of the wavelength of the beam of ultrasonic energy emitted by transducer receiver 12. Generally speaking, the thickness of the beryllium portion 23 of mirror 13 should be at least one wavelength at the minimum transducer excitation frequency. Thus, for medical diagnostic purposes with an ultrasound frequency of 2.5 mHz, the beryllium member 23 should be approximately ⅛ inch thick. The beryllium base portion 23 is coated with a nickel coating 24 which provides a smooth mirror surface and which also reduces or prevents corrosion of the beryllium. The nickel coating is formed by electroless plating of the nickel on the beryllium. The nickel coating should have a thickness of less than 1/10 of a wavelength of the energy being produced by the transducer.

In summary, the scanning head of the present invention reduces the formation of spurious energy beams by providing a mirror comprising beryllium and by moving or scanning the angle of transmission incidence, $\beta$, and the angle of reception incidence, $\alpha$, through a range outside of the inherent angle for the excitation of surface waves on the interface of beryllium. Moreover, the angular relation between transducer passage 15 and transmission and reception passage 18 further reduces the amount of spurious energy which is incident on transducer 12.

While a preferred embodiment has been shown and described, various modifications and substitutions may be made thereto without departing from the spirit and scope of the invention. Accordingly, it is to be understood that the invention has been described by way of illustration and not limitation.

What is claimed is:

1. An ultrasonic scanning head for generating and receiving a scanning energy beam for non-destructive and non-invasive testing comprising:

a housing, said housing being filled with a liquid ultrasound transmission medium;

transducer means positioned in said housing for generating ultrasonic energy in the form of a beam having an axis, said being radiated into said transmission medium;

reflector means being positioned in said housing in the path of the beam of ultrasonic energy radiated from said transducer means to provide for incidence of said energy on a surface of said reflector means at an angle of transmission incidence, said reflector means comprising beryllium; and means for moving said reflector means to thereby vary said angle of transmission incidence of said beam, said moving means constraining the minimum angle of transmission incidence to be greater than the angle at which surface waves are excited at the interface of beryllium and said liquid transmission medium.

2. An ultrasonic scanning head for generating a scanning energy beam for non-destructive and non-invasive testing comprising:
housing means, said housing means defining a transducer passage having a first axis and a transmission and reception passage having a second axis, said passages being in fluid communication and the respective axes intersecting at a point;
a liquid ultrasound transmission medium in said housing passages;
transducer means, said transducer means being positioned within said transducer passage and generating ultrasonic energy in a form of a beam having a beam axis which is coincident with the axis of the transducer passage;
reflector means positioned in the path of the beam of ultrasonic energy radiated from said transducer means to provide for impingement on a surface of the reflector means which is immersed in said liquid medium by said beam at an angle of transmission incidence, a point on said reflector means surface being incident with the point of intersection of the first and second axes, said reflector means being comprised of beryllium; and
means for varying the angle of transmission incidence of said beam, said angle varying means moving said reflector means in at least a first direction about said point of intersection of said axes, said moving means limiting the minimum angle of transmission incidence to be greater than the angle at which surface waves are excited at the interface of beryllium and said liquid transmission medium.

3. The apparatus of claim 2 wherein said transducer means comprises a crystal having a natural focus.

4. The apparatus of claim 2 wherein said reflector means pivots about said point of intersection of said axes.

5. The apparatus of claim 4 wherein said reflector means has a thickness equal to at least one wavelength in beryllium of the minimum ultrasound frequency to be generated by said transducer means.

6. The apparatus of claim 2 wherein said reflector means further comprises:
a nickel coating on said surface of the beryllium, said coating having a thickness which is less than 1/10 of a wavelength in nickel of the minimum ultrasound frequency to be generated by said transducer means.

7. The apparatus of claim 4 wherein said reflector means further comprises:
a nickel coating on said surface of the beryllium, said coating having a thickness which is less than 1/10 of a wavelength in nickel of the minimum ultrasound frequency to be generated by said transducer means.

8. The apparatus of claim 7 wherein said transducer means comprises a crystal having a natural focus.

9. The apparatus of claim 2 wherein said axes intersect at an angle of less than 90°.

10. The apparatus of claim 8 wherein said axes intersect at an angle of less than 90°.

* * * * *